United States Patent [19]

Niolon

[11] Patent Number: 5,171,524
[45] Date of Patent: Dec. 15, 1992

[54] APPARATUS FOR DETECTING CORROSIVE CONDITIONS IN PIPELINES

[76] Inventor: Spencer L. Niolon, P.O. Box 80125, Lafayette, La. 70598-0125

[21] Appl. No.: 242,647

[22] Filed: Sep. 12, 1988

[51] Int. Cl.$^5$ .................. G01N 17/04; G08B 21/00
[52] U.S. Cl. ........................... 422/53; 204/404; 324/694; 340/604; 73/29.05
[58] Field of Search ............... 422/53; 204/1 C, 404, 204/153.11; 324/544, 557, 65 R, 65 CR, 71.1, 72, 664, 694, 696, 700, 718; 340/603–605; 73/29, 304 R, 29.01, 29.04, 29.05; 174/11 R

[56] References Cited

U.S. PATENT DOCUMENTS

| | | | |
|---|---|---|---|
| 3,361,660 | 1/1968 | Chittum et al. | 204/404 |
| 3,639,876 | 2/1972 | Wilson | 422/53 |
| 3,874,222 | 4/1975 | Ladd et al. | 73/40.5 R |
| 4,095,174 | 6/1978 | Ishido | 324/52 |
| 4,319,232 | 3/1982 | Westphal | 174/117 R |
| 4,374,379 | 2/1983 | Dennison, Jr. | 340/604 |
| 4,468,609 | 8/1984 | Schmitz | 324/61 |
| 4,506,540 | 3/1985 | Marsh | 422/53 |
| 4,673,926 | 6/1987 | Gorman | 340/605 |
| 4,752,360 | 6/1988 | Jasinski | 204/404 |

FOREIGN PATENT DOCUMENTS

| | | | |
|---|---|---|---|
| 2725224 | 12/1978 | Fed. Rep. of Germany | 340/605 |
| 1377519 | 9/1964 | France | 340/605 |
| 612102 | 5/1978 | U.S.S.R. | 340/605 |

OTHER PUBLICATIONS

C. E. Bridges and M. A. Clarke, "The Importance of Corrosion Monitoring in Oilfield Systems," Apr. 1979.

Primary Examiner—Robert J. Warden
Assistant Examiner—William H. Beisner
Attorney, Agent, or Firm—Pravel, Gambrell, Hewitt, Kimball & Krieger

[57] ABSTRACT

Apparatus for detecting corrosive conditions in pipelines comprises a wire having an electric potential different from the electric potential of the pipeline. The wire is disposed in the pipeline in a housing which prevents it from coming into contact with a pig used to clean the interior of the pipeline. The wire is spaced from the interior of the pipeline so that it normally is not in direct electrical contact with the pipeline. The wire extends out of the pipeline and is electrically connected to an indicator. The indicator is also electrically connected to the pipeline. When corrosive fluid, such as briny water, is present in the pipeline and comes into contact with the wire and the interior of the pipeline, an electric current is electrochemically produced due to the difference in electric potential between the pipeline and the wire. The indicator detects this current and indicates that corrosive conditions are present in the pipeline. Preferably, a number of wires are longitudinally aligned along the length of the pipeline, with a separate indicator for each wire, such that one can readily tell at what location in the pipeline corrosive conditions exist. The apparatus of the present invention can be used in any pipeline carrying normally non-electrically conductive fluid.

16 Claims, 1 Drawing Sheet

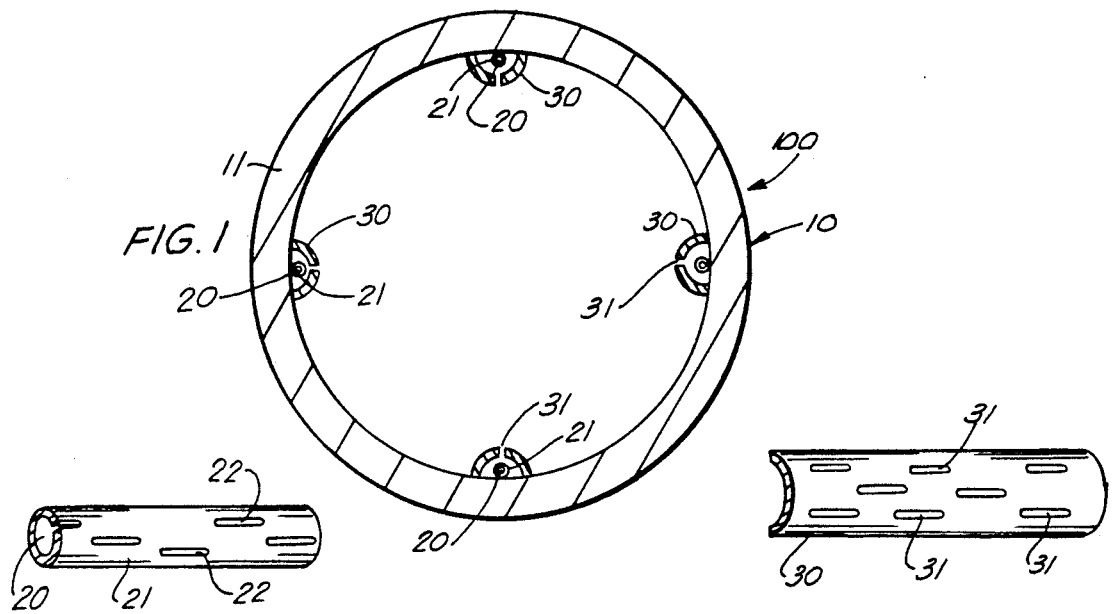
FIG. 1
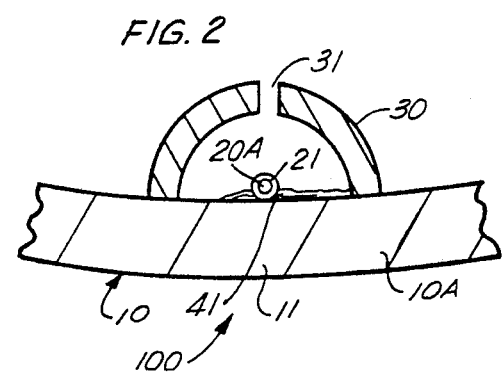
FIG. 2
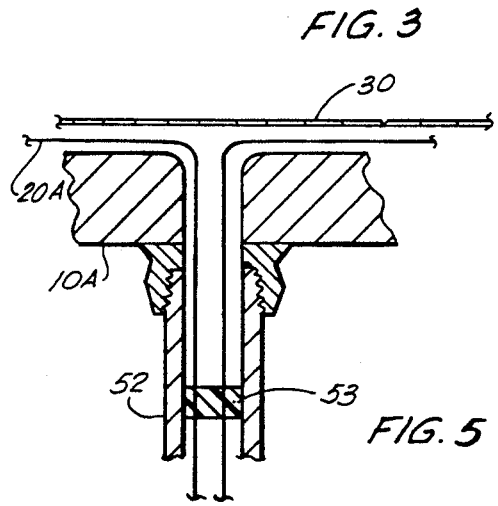
FIG. 3
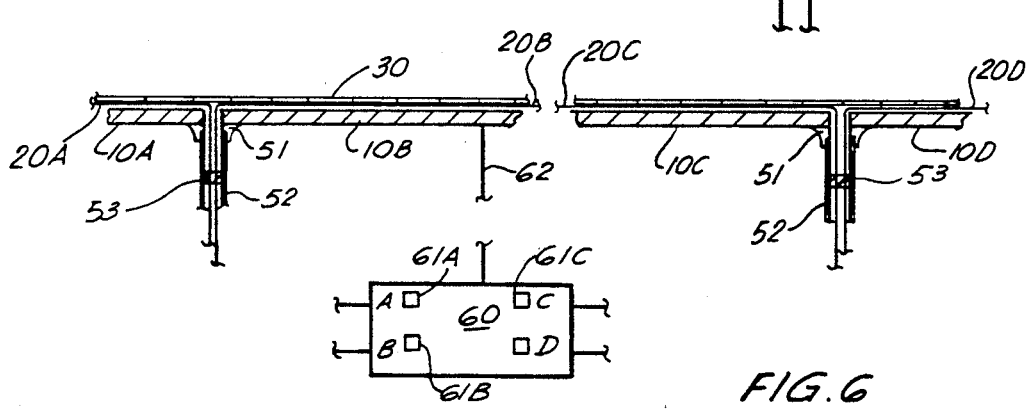
FIG. 4
FIG. 5
FIG. 6

APPARATUS FOR DETECTING CORROSIVE CONDITIONS IN PIPELINES

BACKGROUND OF THE INVENTION

1. Field of the Invention

The present invention relates to corrosion detectors, and more particularly to corrosion detectors for pipelines.

2. General Background

Corrosion of pipelines occurs on the exterior of pipelines and on the interior.

Corrosion of the interior of the pipeline most commonly occurs, in a pipeline carrying gas or liquid condensate, at the bottom of the pipe, where water which condenses out of the gas, or separates from the oil, settles. This water causes the pipe to corrode.

Corrosion of the interior of the pipe also occurs at other locations, such as the "12 O'clock" position (the uppermost part of the interior of the pipe). "12 O'clock" corrosion can occur when a pipeline carrying a liquid is not completely full. Water condenses, out of gas located above the liquid, onto the upper part of the pipe.

Corrosion of pipelines, if undetected, can be a serious problem. If the pipeline carries natural gas, and the pipeline explodes due to corrosion, the results can be disastrous. Also, if the pipeline is carrying petroleum, unchecked corrosion can result in leaking oil contaminating the environment.

To prevent corrosion of the exterior of the pipelines, pipelines are usually painted and/or are attached to a piece of metal having a lower electric potential than the pipeline. The piece of metal acts as a sacrificial anode, accepting free electrons from the pipeline and corroding so that the exterior of the pipeline does not corrode. However, the protection of this anode does not extend through the wall of the pipeline to prevent the pipeline from corroding on its interior.

There is presently no system for effectively preventing corrosion of the interior of pipelines. Sacrificial anodes are not used inside pipelines because they would impede flow of fluid through the pipelines and also because they would get in the way of pigs (in-line scrapers) used to clean the interior of the pipelines. There are, however, a couple of systems which attempt to detect corrosion on the interior of pipelines.

One system utilizes a coupon (a flat, thin sheet of metal) placed inside the pipeline at the "12 O'clock" position. Periodically, the coupon is removed from the pipeline and weighed or otherwise measured to determined how much it (and presumable the pipeline) has corroded.

Another corrosion detection system presently in use is a linear polarization probe system. That system comprises placing a thin wire in the pipeline. A meter is connected across the ends of the wire. As the wire corrodes, the resistivity of the wire increases, and this increased resistivity is measured by the meter.

While the two detection systems sound useful in theory, in practice their application is limited to points at which the pipeline is above ground. Further, if corrosion is taking place at the bottom of the pipeline, but not at the top, these systems may not detect it. Moreover, corrosion may take place underground. If the systems are only used on above-ground sections of pipeline, they will likely fail to detect corrosion occurring in underground sections of the pipeline.

SUMMARY OF THE PRESENT INVENTION

The present invention includes an apparatus for detecting corrosion in pipelines. The apparatus includes a wire, having an electric potential different from that of the metal making up the pipeline, disposed in the pipeline. The wire is normally electrically insulated from the pipeline, and is disposed in a protective housing so that it will not be harmed by pigs used to clean the pipeline. The wire extends out of the pipeline and is connected to an indicating means. If impure water or some other electrically conductive material comes into contact with both the wire and the pipeline, a current is induced, due to the difference in electrical potential between the wire and the pipeline. The indicating means detects this current, which indicates to an observer the presence of a corrosive fluid in the pipeline. Preferably, a number of longitudinally aligned wires are placed along the length of the pipeline so that the indicating means can indicate at what location in the pipeline corrosive conditions exists. Also, the wires may be placed in more than one radial location in the pipeline so that whether corrosive fluid gathers at the bottom of the pipeline, at the "12 O'clock" position, or elsewhere, it will be detected.

The present invention can be used in any pipeline carrying normally non-electrically condutive fluid.

The objects of this invention will be readily apparent to those skilled in the art from the detailed description and claims which follow.

BRIEF DESCRIPTION OF THE DRAWINGS

For a further understanding of the nature, objects, and advantages of the present invention, reference should be had to the following detailed description, taken in conjunction with the accompanying drawings, in which like parts are given like reference numerals, and wherein:

FIG. 1 is a section through the apparatus of the preferred embodiment of the present invention;

FIG. 2 is a perspective, partially cut-away view of a piece of wire used in the preferred embodiment of the present invention;

FIG. 3 is a perspective, partially cut-away view of a wire protector in accordance with the preferred embodiment of the present invention;

FIG. 4 is a detail of the apparatus of the present invention taken along the lines 4—4 in FIG. 6;

FIG. 5 is a detail of the apparatus shown in FIG. 6; and

FIG. 6 is a cut-away partial view of an embodiment of the present invention.

DETAILED DESCRIPTION OF THE PREFERRED EMBODIMENT

Apparatus 100 for detecting corrosive conditions in pipelines comprises a wire 20 (FIGS. 1 and 2) having an electric potential different from the electric potential of pipeline 10. One or more wires 20 can be placed in pipeline 10, four being shown in FIG. 1. Insulation 21 on wire 20 acts as a means for normally preventing direct electric contact between wire 20 and pipeline 10. Openings 22 (see FIG. 2) in insulation 21 allow electrical contact, under the proper conditions, to be made between wire 20 and pipeline 10, as will be discussed further. Insulation 21 may comprise, for example, a non-electrically conductive sheath, such as a plastic sheath.

Wires 20 are preferably disposed in arcuate housings 30, which act as means for preventing physical contact between wire 20 and a pig (an in-line scraper—not shown) used to clean out pipeline 10. Housings 30 have openings 31 (see FIG. 3) to allow fluid in the rest of pipeline 10 to freely flow into contact with wire 20. Housing 30 can be metal (preferably of the same type as pipeline 10 to prevent electrochemical reaction between the two) and may be tack welded with welds 32, as shown in FIG. 4, or attached to pipeline 10 in any suitable fashion. FIG. 6 shows wires 20A-20D, disposed in sections 10A-10D of pipeline 10, connected to a PC (printed circuit) board 60, which acts as an indicating means. In FIG. 6, only the wire and housing on the bottom of pipeline 10 are shown (in many cases it will suffice to only have the corrosive conditions detection apparatus on the bottom of a pipeline—occasionally, however, one may use wires on more locations to detect "12 O'clock" corrosion and corrosion in other places).

Wires 20A and 20B are disposed in sections 10A and 10B, respectively, of pipeline 10. Wires 20A and 20B pass through the wall 11 of pipeline 10 through a port 50 disposed in wall 11 adjacent the juncture of sections 10A and 10B. A similar port 50 is disposed in wall 11 adjacent the juncture of sections 10C and 10D. A threaded coupling 51 is welded or is otherwise attached to the outside of pipeline 10 adjacent port 50. A tube 52 is threadedly inserted into coupling 51. Tube 52 has a gasket 53 therein, to prevent the contents of pipeline 10 from exiting pipeline 10 via port 50. Wires 20A and 20B travel from sections 10A and 10B, respectively, of pipeline 10, through port 50, threaded coupling 51, tube 52 and gasket 53 to corrosion indicators 61A and 61B, respectively, on PC board 60. Wires 20C and 20D are similarly connected to corrosion indicators 61C and 61D, respectively.

A wire 62, which is in electrical contact with pipeline 10, is also connected to PC board 60. Corrosion indicators 61A-61D indicate whether corrosion is occurring in sections 10A-10D, respectively, of pipeline 10, as will be described below.

The operation of apparatus 100 will now be described in conjunction with FIGS. 4-6.

In FIG. 4, pipeline 10 is transporting compressed natural gas under pressure. Water 41, which condenses out of the natural gas, gathers at the bottom of section 10A of pipeline 10. Water 41 has impurities therein, such as salt. If undetected, the water 41 would corrode pipeline 10. The impurities which make water 41 corrosive make it electrically conductive, such that wire 20A and section 10A of pipeline 10 become electrically connected to one another. As mentioned before, wires 20 and pipeline 10 have different electric potentials.

When wire 20A and section 10A of pipeline 10 come into electrical contact via water 41, current is electrochemically produced, and flows through corrosion indicator 61A, causing indicator 61A to indicate that corrosive conditions are present in section 10A. Depending upon which has a smaller electric potential, either pipeline 10 or wire 20 corrodes. Preferably, wires 20 have a higher electric potential than pipeline 10, so that pipeline 10, not wire 20, corrode when they are electrically connected; otherwise wires 20 would need to be replaced relatively often. For example, when the pipeline is made of iron, wire 20 is preferably made of copper. Since copper has a higher electric potential than iron, pipeline 10, not wire 20, will corrode, so wire 20 need not be replaced often.

Wire 20 should not be used without insulation 21 or a similar spacer to keep it from contacting pipeline 10. Normally, in the absence of briny water or some other electrolytic solution, no corrosion would occur where wire 20 meets pipeline 10. However, if a current is induced on the outside of pipeline 10, and wire 20 is in electrical contact with pipeline 10, reduction would occur at wire 20 and oxidation (corrosion) at pipeline 10.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. Apparatus, for detecting corrosive conditions in pipelines, comprising:
   a) a wire for placement in a pipeline, the wire having an electric potential different from the electric potential of the pipeline;
   b) means for preventing direct electrical contact between the wire and the pipeline;
   c) means to prevent the wire from coming into contact with a pig; and
   d) indicating means for indicating when current flows between the wire and the pipeline.

2. The apparatus in claim 1, wherein the wire has a higher electric potential than the pipeline.

3. The apparatus in claim 1, wherein the means for preventing direct electrical contact between the wire and the pipeline comprises insulation on the wire.

4. The apparatus in claim 1, wherein the means for preventing direct electrical contact between the wire and the pipeline comprises a non-electrically conductive sheath on the wire, the sheath having openings therein.

5. The apparatus in claim 1, wherein the means to prevent the wire from coming into contact with a pig comprises a housing having openings therein.

6. The apparatus in claim 5, wherein the housing is secured to the interior of the pipeline.

7. The apparatus in claim 6, wherein the housing is secured to the bottom of the pipeline.

8. The apparatus in claim 7, further comprising a second housing secured at the top of the pipeline.

9. The apparatus in claim 1, wherein the apparatus comprises a plurality of wires aligned longitudinally in the pipeline, the indicating means having indicators for indicating at which wires corrosive conditions are present.

10. The apparatus of claim 1, further comprising port means on the pipeline for allowing the wire to pass from the interior of the pipeline to the indicating means.

11. The apparatus of claim 1, wherein the wire is placed longitudinally in the pipeline.

12. The apparatus of claim 8, further comprising a second wire in the second housing.

13. Apparatus, for detecting corrosive conditions in pipelines, comprising:
   a) a wire for placement longitudinally in a pipeline, the wire having an electric potential different from the electric potential of the pipeline;
   b) means for preventing direct electrical contact between the wire and the pipeline;
   c) indicating means for indicating when current flows between the wire and the pipeline; and d) means to prevent the wire from coming into contact with a pig.

14. The apparatus in claim 13, wherein the means to prevent the wire from coming into contact with a pig comprises a housing having openings therein.

15. Apparatus, for detecting corrosive conditions in pipelines, comprising:
  a) a wire placed longitudinally in a pipeline, the wire having an electric potential different from the electric potential of the pipeline;
  b) means for preventing direct electrical contact between the wire and the pipeline;
  c) indicating means for indicating when current flows between the wire and the pipeline; and
  d) means to prevent the wire from coming into contact with a pig.

16. The apparatus in claim 15, wherein the means to prevent the wire from coming into contact with a pig comprises a housing having openings therein.

* * * * *

UNITED STATES PATENT AND TRADEMARK OFFICE
CERTIFICATE OF CORRECTION

PATENT NO.   : 5,171,524
DATED        : December 15, 1992
INVENTOR(S)  : Spencer L. Niolon It is certified that error appears in the above-identified patent and that said Letters Patent is hereby corrected as shown below:

On title page, add the following:

-- [73]  Assignee: Marathon Oil Company,
                   Findlay, Ohio --.

Signed and Sealed this

Fifth Day of July, 1994

Attest:

BRUCE LEHMAN

Attesting Officer

Commissioner of Patents and Trademarks